United States Patent [19]

Deffeyes et al.

[11] 4,004,917

[45] * Jan. 25, 1977

[54] ACICULAR METALLIC POWDERS PRODUCED FROM THE ORGANOMETALLIC SALTS

[75] Inventors: Robert J. Deffeyes; Wesley R. Tyler, both of Arlington, Tex.

[73] Assignee: Graham Magnetics Incorporated, Graham, Tex.

[ * ] Notice: The portion of the term of this patent subsequent to Sept. 30, 1992, has been disclaimed.

[22] Filed: July 11, 1975

[21] Appl. No.: 595,066

Related U.S. Application Data

[62] Division of Ser. No. 401,636, Sept. 28, 1973, Pat. No. 3,909,240.

[52] U.S. Cl. .............................. 75/.5 AA; 75/.5 A; 148/105
[51] Int. Cl.² ......................................... C22B 23/04
[58] Field of Search ............... 75/.5 R, .5 A, .5 AA; 148/105

[56] References Cited

UNITED STATES PATENTS

| 3,574,685 | 4/1971 | Haines | 75/.5 AA X |
| 3,607,218 | 9/1971 | Akashi | 75/.5 AA |
| 3,803,191 | 4/1974 | Ehrreich | 423/594 X |
| 3,902,888 | 9/1975 | Aonuma et al. | 75/.5 AA |

*Primary Examiner*—Arthur J. Steiner
*Attorney, Agent, or Firm*—Andrew F. Kehoe; Robert A. Cesari; John F. McKenna

[57] ABSTRACT

Improved processes and products based on the discovery that metal atoms in complex relationship with complexing agents can be used to moderate the formation of organic salt seed crystals which promote an exceptionally well-ordered acicular growth of organometallic salts such as oxalates of the metal. Some acicular, i.e. needle-like, products have particular utility for being reduced to ferromagnetic metal particles which retain a surprisingly large degree of acicularity and possess extraordinarily favorable properties for use in magnetic recording applications.

9 Claims, 7 Drawing Figures

ACICULAR METALLIC POWDERS PRODUCED FROM THE ORGANOMETALLIC SALTS This is a division of application Ser. No. 401,636, filed Sept. 28, 1973, now U.S. Pat. No. 3,909,240.

BACKGROUND OF THE INVENTION

During recent years, there has been a great deal of research and development activity directed to making small metallic particles, especially small ferromagnetic metallic particles for use in magnetic tapes and the like. It will be understood that many of the processing improvements developed during work on magnetic particles will also have an advantage in making non-magnetic metal particles. This is generally true to the extent that such parameters as uniform particle size, optimum particle size, a discrete predictable shape, favorable bulk density or surface area, and other such desirable physical properties are advantageous in metallurgical compounding work, in making catalysts, etc. Also, the reproducible, highly ordered morphology of particles produced by the process of the invention is believed to be of general importance. Thus, although the basic inventions described herein were initially reduced to practice during work directed towards making improved magnetic powders, the emphasis on magnetic particles (and the extraordinary properties thereof) in this application should not be interpreted as an intent to waive coverage on other novel powders or on the novel organometallic salt precursors prepared according to the instantly-disclosed process and from which non-magnetic powders can be prepared.

Considerable emphasis on making high performance magnetic powders has focused, over the last ten or fifteen years, on making high-performance cobalt-based metal particles. There are a number of properties such particles should have and they include the following:

High Coercivity and, preferably, the temperature dependence of the coercivity value should be minimized.

High Sigma Value — usually denotes high metal content, i.e. a minimum amount of surface oxide contamination or minimal use of non-magnetic, coercivity-inducing additives into the crystalline structure.

High Squareness — the squareness of the hysteresis loop should be maximized. Unless otherwise noted, this squareness is measured in a field of 2000 oersteds.

Reasonable particle size — very small acicular particles, say, those having an average length of as low as 0.05 microns will have enormously large surface areas and will be difficult to disperse in desirable polymeric binder media to form coatings required in manufacture of magnetic tape. (On the other hand, for many purposes, it is well to be able to control the process to achieve much smaller particles.)

High Acicularity — needle-like metal particles have been difficult to produce. Even when highly acicular organometallic salts are used, the resulting metal is usually less acicular than is desired.

Good Particle Size Distribution — the above-mentioned average particle size will have little value if the particulate product comprises an excessive surface area due to many very small particles. (On the other hand, larger than average particles may cause problems in metallurgical work.) Moreover, a relatively narrow particle size range is believed, on the basis of work described herein, to provide favorable magnetic properties such as an excellent switching-field distribution and avoidance of bothersome D.C. saturation noise effects in magnetic memory processes such as those utilizing magnetic tapes.

Stability over a period of time — earlier work has resulted in making particles that degraded with respect to magnetic and chemical properties in an undesirably short time.

Other parameters will be discussed in the body of this application.

There have been many attempts to produce improved magnetic metallic particles for incorporation into magnetic coatings. Many of them have involved the decomposition of metal carbonyl or other covalently-bonded compounds. For example, see U.S. Pat. Nos. 3,228,882 and 3,228,881 to Harle et al and Thomas, respectively.

Other such processes have involved the use of borohydrides as reducing agents for metal ions in solution and the subsequent precipitation of the metal powder. Such borohydride type processes are disclosed in such patents as U.S. Pat. Nos. 3,206,338 to Miller et al and 3,661,556 to Jolley et al.

More promising work appears to be the formation and reduction of organometallic salts of carboxylic acids such as metal oxalates and the like. Some such work is described in such U.S. Pat. Nos. as 3,186,829 to Landgraf, 3,574,683 to Johnston, and 3,317,574 to Morita et al. The most pertinent of this work appears in the commonly-owned and co-pending application U.S. Pat. Ser. No. 228,387 filed on Feb. 22, 1972 by Ehrreich and Reti. In this work, the use of a resinous coating envelope over the particles during reduction of an oxalate salt did result in a product having an excellent combination of squareness, coercivity and sigma value.

However, even the powder products produced by the Ehrreich-Reti process have limited commercial utility because of problems associated with stability of sigma value under relatively high humidity and temperature. These powder materials, when incorporated into magnetic tape, also tended to produce a "noise" about certain narrow wavelengths and, as a consequence, was not desirable for some magnetic tape applications.

It will be evident that the discoveries disclosed herein will be applicable generally to the work of those who have produced powders from organometallic salt particles. That process is characterized by a thermal step wherein the organic component of the salt decomposes directly to gaseous by-products leaving a metallic powder residue behind.

Although it had been known to reduce organometallic salts such as oxalates and the like in a thermal reactor for the purpose of obtaining metal particles, the primary concern had been to avoid such high temperatures as will result in excessive sintering of the particle and chemical reactions which will produce excessive oxide content in the finished particle. Thus, for example, control of sintering is one object of the process for coating metal-bearing organometallic particles with an inert material before and during reduction to the metal powder. That process is described in a commonly-owned and co-pending U.S. patent application Ser. No. 367,461 filed on June 6, 1973, by Ehrreich and Reti. That process is particularly advantageous because it results in particles having surprisingly desirable magnetic properties. In any event, the aforesaid discovery by Ehrreich and Reti that materials coated with resins could result in markedly improved magnetic properties stimulated further work in the development of improved processes with the general intent of further optimizing the potential magnetic properties, especially with respect to high acicularity, freeness from DC noise manifestation when incorporated in magnetic tape.

In a hindsight review of fields of art which have some relationship to the invention, the following art has been uncovered:

U.S. Pat. No. 3,046,158 discloses the use of acicular seed crystals of iron oxide which seeds are subsequently used as growth sites for production of acicular iron oxide. Two aspects of this patent are particularly noted: the growth upon the seed in no way contributes to acicularity. All acicularity is contributed by the seed itself; future growth in no way accentuates or preserves the acicular character independently of the pre-existing acicular nature of Fukada's seed. Secondly, the material being grown on the seed is the magnetic powder, not a non-magnetic precursor thereof comprising only a minor volume of metal.

U.S. Pat. No. 2,558,304 discusses the use of "crystal growth directors" which form complexes with hydrated iron oxide. The growth directors were used during oxidation of ferrous compounds to make iron oxide pigments for use in paint and the like.

In The Physics of Magnetic Recording by C. D. Mee (North Holland Publishing Company, Amsterdam, 1968), it is disclosed that certain acicular magnetic particles were made by Luborsky (at pages 196–198). This epic attempt to provide magnetic particles of ideal properties was thwarted by the necessity of using special techniques which inherently resulted in low sigma values of the products.

U.S. Pat. No. 3,740,266 describes broad range of acicular metal particles; applicants know of no practical way to produce acicular metal particles from most of the alloys described therein. Most of the specific art cited involve use of large quantities of non-ferromagnetic dopes, e.g. 10–40 mole percent of Mn, Zn, Sn, Cu or Pb; or use of alkaline earth metals or use of very small quantities of cobalt.

Other art which, when superficially examined, seems to relate to the product aspect of the invention is the U.S. Pat. No. 3,228,882 to Harle et al. This discloses highly acicular structure but the structure is not formed of acicular metal particles. It is formed of very small, nearly spherical, metal particles which are incorporated in — and separated by — an acicular matrix of resin. Such particles have a very low sigma value (on a volume basis) and cannot be loaded into magnetic tape formulation in suitable quantity.

U.S. Pat. No. 3,661,556 to Jolley at al shows complexing agents in an aqueous medium in which metal powder product is formed by reduction of metal salts such as borohydride salts. Jolley et al disclaim knowledge of how their mechanism works, but suggest it works by preventing the precipitation of ferric oxide during the formation of the metal. That invention teaches nothing about the utility of similar compounds in the formation of an organometallic salt which is to be collected as a solid and only later is used as a precursor to metal formed by a high-temperature reduction process; i.e. that invention teaches nothing about a process of the type to be described below. Moreover, there are inherent problems associated with the Jolley et al process: e.g. lack of high squareness, even when there is substantial accularity, and relatively high non-magnetic-metal content, which prevent the products thereof from having the unusually excellent and novel magnetic properties of the powders of the invention which will be described below.

SUMMARY OF THE INVENTION

It is a principal object of the invention to provide an improved process for making metal powders with a high degree of control over the morphology of the powders and for making novel organometallic salt precursors of such powders.

It is a further object of the invention to provide improved metal powders, especially improved ferromagnetic powders for use in magnetic applications.

Another object of the invention is to provide improved magnetic-information storing articles such as magnetic tapes and the like.

Another object of the invention is to make small, novel organometallic salt particles of a more advantageous shape and advantageously-ordered arrangement of atoms.

Still another object of the invention is to provide a means for avoiding the use of resin-type encapsulating materials during reduction of metallic salts to metallic powders.

Another object of the invention is to provide a means for minimizing the cost of providing acicular organometallic crystals and products produced therefrom.

It is a further object of the invention to provide an improved process for making catalytic metal compositions and the improved compositions themselves and processes utilizing these compositions.

Other objects of the invention will be obvious to those skilled in the art on reading the instant application.

The above objects have been substantially achieved by utilizing the discovery that it is advantageous to prepare highly acicular organometallic salts from organic acids and a metal cation by initiating the precipitation or growth of the salt in the presence of a quantity of complexing agent. The resulting metal complex (or metal complexes) apparently controls (by some directing phenomena, which may involve rate or stereochemical phenomena) the morphology and shape assumed by the embryonic and growing organometallic salts. The method is especially advantageous when used to promote the growth of highly acicular salts.

One frequently-noted visual feature of the aciclic organometallic salts precipitated by the process of the invention is the pearlescence or iridescence of the precipitate as it forms with stirring. Moreover, a distinct pinkish color seems to predominate in cobalt-based salt systems whereas in the prior art such systems tended to exhibit a brownish tinge. It is believed these visual features are primarily due to the uniformity of the organometallic salt's particle size and the acicular nature of the particles.

Indeed, when used to produce acicular organometallic salts such as oxalates comprising a major portion of cobalt in the metal portion thereof, it has been found that the crystalline arrangement of the salt provides, upon suitable reduction to the metal, very substantial improvements in the magnetic properties of the metal. Surprisingly, the highly acicular properties of the initial precipitate (which we may call a seed) are transmitted to the organometallic salt grown from the seed and also to the metallic powder reduced from this organometallic salt. This appears in the first instance at least, due to growth of a fasces-like organometallic salt which can "splinter" on reduction. The improvements in ferromagnetic metal powders include extremely high squareness ratio of the hysteresis loop, and low DC noise, and high magnetic output from tapes produced therefrom. Such metal particles, when compared to their counterparts formed by the most favorable prior art procedures, also exhibit improved chemical stability; improved switching fields characteristics; improved coercive force, sigma value and squareness as a combination of properties; and an important improvement in the temperature dependence of the coercive force. The latter improvement is believed to be caused by the relative dominance of shape anisotropy over crystalline anisotropy.

In one embodiment of the invention, the initial precipitation of seed crystals takes place in the same medium in which the primary growth of organometallic salt is to occur. In such a situation, it is usually desirable to utilize a liquid medium wherein the solubility of the organometallic salt is less than its solubility in water. This is conveniently achieved by adding an organic solvent to the water. Such water-soluble solvents as acetone, lower alkyl alcohols like ethanol, and the like, are entirely satisfactory, and those skilled in the art can select many other such readily-available solvents for use if they wish to do so.

In another embodiment of the invention, seed crystals may be formed in a first medium containing the complexing agent and, advantageously, a water-solvent medium and then transferred to the primary crystal-growing solution. One advantage of this latter procedure is that, when the complexing agent is properly selected, the population density of seeds or seed-promoting complexes in the first medium can be so high that a very small volume of the medium containing the seeds or seed-promoting complex can be used to initiate the growth of crystals in the primary crystal-growing solution. This is true even when the medium for the primary crystal-growing step is entirely aqueous. Thus, it is seen that this embodiment of the invention can be carried out using a relatively small amount of organic solvent and complexing agent.

It is possible, of course, for the complexing agent to act as a solubility-limiting material also. Indeed ethylene glycol is illustrative of one compound that is advantageously utilized in such a dual role.

The term complexing agent herein is used to cover chemical compounds which associate with metal ions in the reaction solution. Cobalt's tendency to form such associations is well known. The association may be via coordinate bonds, hydrogen bonds, or other such forces; the resulting compound may be looked at as a coordination complex, a chelate or more particularly described by some other terminology. Among the useful complexing agents are organic compounds such as polyhydroxy compounds including sugars, hydroxy carboxylic acids, dicarboxylic acids, and the like. The amino and hydroxy carboxylic acids advantageously have an amine or hydroxyl group adjacent the carboxy group. Inorganic compounds can also be used. Those bearing the ammonium ion are easily utilized in suitable complex formation. For the purposes of the invention the particular metal complex should at least partly be dissociable in the reaction medium. There would be no point in permanently sequestering the metal to prevent its mobility to the embryonic seed crystal, nor would there be any point in dropping the metal out of solution in an insoluble complex precipitate. On the other hand, if the complex is so readily dissociable in the particular medium in which it is used that only an inoperable complex is existant, then the complexing agent or the medium must be changed to make the complexing agent useful. These considerations will be obvious to chemists reading this disclosure. However, they are made explicit here because of the physical impossibility of listing all of the solvent systems and complexing agents which could find use in the process of the invention.

Among complexing agents advantageously used in the invention are included such compounds as sugars, especially sugars like glucose, sucrose and the like; glycols such as ethylene glycol and the like; glycerine and the like. Dicarboxylic acid complexing agents, e.g. phthalic acid and the like, are also useful. Indeed, some of the more advantageous aliphatic complexing agents are such aliphatic acids as tartaric acid, citric acid and the like. Other such acids include glycolic, hydroxy lactones such as ascorbic acid, lactic, hydroxy-butyric, mandelic, glyceric, malic, and the like. Ethyl alpha hydroxy butyrate is believed to be another effective complexing agent as is ethylene diaminetetracetic acid. In general, the more advantageous organic complexing agents appear to be those with two or more hydroxy groups, two or more amino groups, a hydroxy group with an adjacent carboxyl group or an amino group with an adjacent carboxyl group. But other such sites can interact with a cobalt ion to form a complex as is known in the art. Using the above teachings, and the vast amount of pre-existing literature already known to the art and which relates to cobalt-complexing agents, it is expected all skilled in the art will be able to select many additional complexing agents; all such materials, including such sometimes "chelating" agents as diethylene triamine, and the like are intended to be covered by the term "complexing agent" as used in this application.

In many embodiments of the invention, the use of complexes seems to result in a catalytic-like effect whereby reactions are promoted which do not take place, or take place relatively poorly, in the absence of the complex-promoted growth of seed crystals.

The cobalt-bearing organometallic salts formed of carboxylic acids by the aforesaid complex-utilizing seeding procedure are characterized by great acicularity. They tend to form in what appears to be elongate fasces which, on reduction to the metal, tend to splinter along the direction of the axis of the fasces and form elemental cobalt metal particles of a more highly acicular and ordered crystalline structure than has been achieved heretofore. Most important, it appears that this acicularity of shape also manifests itself in an improved dominance of shape anisotropy or crystalline anisotropy characteristics in magnetic behavior of the particles.

Anisotropy is the non uniformity, or directional dependence, of the magnetic properties. It is anisotropy that gives rise to the coercive force. Anisotropy can be caused by many different factors. In the kind of magnetic particles described herein, the dominant anisotropy factors are shape anisotropy and crystalline anisotropy. Shape anisotropy arises from the particle being unequal in length and diameter. Particles with high shape anisotropy are desirable because they can be oriented in a magnetic tape system and because their magnetic properties are not substantially influenced by changes in temperature. Crystalline anisotropy relates to anisotropies in the crystalline structure of the magnetic particle. The coercive force of a particle which derives its magnetic properties from crystalline anisotropy will change as about the 10th power of the absolute temperature. Thus, the crystalline anisotropy can be distinguished from shape anisotropy by measuring the coercive force at room temperature and at some reduced temperature. Measurements made at about 25° C and at liquid nitrogen temperature reveal the products of the instant invention to have unusually stable magnetic properties over a broad range of temperatures.

Oxalic salts are the preferred salts for use in making cobalt-bearing metals of the invention. They tend to give the cleanest reduction step because of the stoichiometric balance of the cobalt oxalate molecule whereby the nonmetallic reaction products of the oxalate are entirely gaseous. However, the process of the invention can also be carried out using such low molecular weight carboxylate salts as formates, succinates, acetates, malonates, maleates, and the lower alkyl derivatives of such compounds.

The metal component of the organometallic salt is advantageously derived from such organo radicals as those normally associated with weak acids, i.e. acids weaker than the acid formed with water by the organo component of the organometallic salt being synthesized. These include such compounds as formic acid, acetic acid, and other such acids known to the art. It should be realized that the use of such metal salts of weak acids is not mandatory. Any increased cost in materials and process can be measured against the value of the improved magnetic properties in any application. It is to be emphasized that inorganic salts, e.g. cobalt nitrate, are also suitable.

The advantage in magnetic properties, formed by reduction of organometallic particles so formed, seems primarily to manifest itself in the advantageous squareness. This is not to demean the other novel advantages of the particles formed by the invention; but only to emphasize that squarenesses of 0.60 and higher, which have been extremely elusive in formation of truly acicular cobalt-based metal particles, appear to be directly related to the crystalline order in which the organometallic salts are formed prior to the reduction step.

A particle described herein as "cobalt-based" or "predominantly cobalt" means a particle having over 50% cobalt by weight.

It should also be emphasized that the "high" proportion of unusually acicular metal particles in the mass of particulate product, i.e. acicular predominantly cobalt particles having length to width ratios from about 3:1 and advantageously from 10:1 to 20:1 and above have apparently contributed a still further increase in the dominance of shape anisotropy over crystalline anisotropy. This attribute of the invention, in effect, can be utilized to make the coercivity of the metal powder product substantially temperature independent, i.e. coercivity change of less than 100% between −196° C. and 20° C. Indeed, this change in coercivity can be kept below 40% and even below 20% by the process of the invention. These low increases in coercivity with temperature are believed to be novel for predominantly cobalt particles of the type described.

Even more important, it has been discovered for the first time that acicular metal particles containing substantial quantities of nickel can be made by the process of the invention, e.g. by using a cobalt oxalate seed crystal in growing a cobalt-nickel oxalate and then reducing it. For example, it is not believed that any highly acicular metal particle, i.e. having a length-to-width ratio of 3:1 or better, and containing as much as 8% nickel has ever been manufactured in a form having desirable ferromagnetic properties. But, by the process of this invention nickel, in quantities of from 8 to about 30% by weight, can be incorporated into acicular cobalt-based particles having length-to-width ratios of up to 20 − 1.

Heretofore it has not been possible to make cobalt-based magnetic particles having squarenesses as high as 0.72, achieve magnetic coercivities over 500 oersteds and volumetric sigma values over about 900 emu per cubic centimeter while achieving the shape anisotropy and size characteristics advantageous in magnetic tapes and like applications. Indeed, squareness values of about 0.7 to 0.88 have been achieved, with particles formed of 50% and more of cobalt metal, by the process of the invention.

Another important aspect of the invention is that it provides, in some of its embodiments, a means to avoid the use of the coatings taught by Ehrreich and Reti in U.S. Pat. Ser. No. 228,387, but yet achieve excellent magnetic properties.

However, if one wishes to obtain the maximum sigma obtainable using such a coating-free process, it may be necessary to sacrifice squareness and some of the higher coercive force that can be achieved using the preferred coating procedure.

A particularly interesting aspect of the above process and products produced thereby is that proper conditions are selected so that extremely small organometallic crystals are formed. A very small volume of such crystals, suitably handled and utilized in the medium in which they were formed, can be used to seed the growth of other suitably acicular and suitably-sized crystals of organometallic salt. The particular value of this phenomenon is that the seed crystal, precipitated with the complexing agent and in a low-solubility medium such as formed by ethanol and water, is effective to initiate growth of the greater mass of oxalate in an aqueous medium containing little or no solubility-modifying solvent for reducing the solubility of the organometallic salt. Thus, utilization of this seeding step markedly reduces time, and cost and markedly increases the convenience of the organometallic salt manufacturing operation. It is advantageous, when forming a seed crystal by pouring a metal-bearing solution into a carboxylate-bearing solution to have some complexing agent, say a sugar, in each solution. It is also advantageous to have a solvent such as alcohol in each solution. Usually, the "seed-causing" complexing agent is carried in the metal-bearing solution.

In general, the complexing agents that are most useful in this seeding technique are those that permit the making of seed crystals of an extremely small particle size. Some of these complexing agents are citric acid, hexamethylene-tetramine, tartaric acid, ascorbic acid, and ammonium nitrate. Others include ethylene diamine tetramine, tartaric acid, maleic acid, and alanine.

One way of evaluating a complexing agent for use in seed-type processes is to measure the viscosity of a seed material produced thereby. A screening test made with a Brookfield Synchroelectric Viscometer Model RVF at a speed setting of 4, and No. 2 spindle (a No. 3 spindle may be used for the more viscous materials) has proved helpful.

The spindle is allowed to run for 60 seconds at speed before the reading was taken. In general, it is believed that materials which yield a reading below 5 are much less likely to be advantageous for use as seed materials than those which yield a reading above 5.

The temperatures at which the organometallic salt precipitations of the invention can be carried out vary widely but usually will be most convenient between 0° F. to 200° F. The optimum temperature, like the optimum solvent system, will usually depend on the solubility and stability of the complex itself. With most complexing agents it seems desirable to operate at lower rather than higher temperatures, for example temperatures closer to 10° to 50° F. are usually better than between 100°–140° F. It is not certain whether the advantage is due to the improved complexing action at lower temperatures or to changes in solubility.

There have been no significant disadvantages experienced with this seeding technique as opposed to the direct, i.e. one-medium process.

It should be understood, by those skilled in the art on reading this disclosure, that the required complexes can, in addition to being formed in place by bringing the metal cation and complexing agent together in a solution, be formed by bringing a solid reaction product comprising the metal cation and complexing agent into the solution wherein the organometallic salt is to be formed. For example, a solid product of cobalt and citric acid is a suitable solid precursor for soluble complexes which are useful in the process of the invention. The citric acid radical apparently provides, in solution with cobalt, the required complexing agent or agents.

The mechanism by which the process of the invention operates does not seem to be explained by reference to conventional seeding technology. By "operation" in this paragraph is meant operation in the chemical process sense; no reference to the extraordinary magnetic properties and the unobviousness of using the disclosed process to obtain them is intended). It may be that the complexing agents used form a plurality of species of complexes with the selected complexing agents, that these different complexes have different solubilities, that some of them tend to initiate crystal growth while others tend to moderate the rate or extent of growth once it is initiated. In any event, patentability of the invention herein is not predicated on an understanding of the precise physico-chemical mechanism of the reactions involved therein.

In general, the kinds of agents used by Jolley et al and described in Columns 2 and 3 of U.S. Pat. No. 3,661,556 are useful with the process of this invention when utilized with properly balanced solvent medium. That disclosure is incorporated by reference in this specification. Martel and Calvin, in "Chemistry of the Metal Chelate Compounds," (Prentice-Hall, Incorporated, New York, N. Y., 1950, pp. 514 – 558) also provide useful information for those who wish to use complexing agents other than those specifically described herein. Nothing in this paragraph should be construed to imply that the function of the chelating agents of Jolley et al is the same as the complexing agent of the instant invention. The term chelate connotes a capture of undesirable species and Jolley et al believe their metal-forming process works that way. Applicants believe that the complexing agents of their invention have a positive effect on promoting the favorable crystal growth of their organometallic salts; although, of course, the actual mechanism by which such beneficial results are achieved remain unknown.

In the Drawings

FIG. 1 is an integrated hysteresis loop;

FIG. 2 is a similar loop but with an unintegrated value of the magnetic moment with time (a $dM/dt$ curve); and FIG. 3 shows a series of hysteresis loops achieved for a single sample of particles under varying applied magnetic fields.

Figure 6:
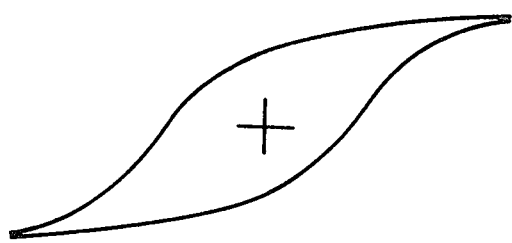
Figure 7:

FIGS. 6 and 7 are similar to 4 and 5 but represent 85 cobalt-15% nickel particles of the above-mentioned Ehrreich-Reti invention, the best known prior art in the statutory sense.

The abscissa of the graphs of FIGS. 1, 3, 4 and 6 ranges from −2000 to +2000 oersteds and represents the 2000 oersted magnetic field in which the measurements are carried out. The ordinate can be considered as arbitrarily selected to aid demonstration of the difference between tested specimens. (The abscissa in FIGS. 2, 5 and 7 is reversed, and reads from +2000 to −2000, left to right.)

The drawings must be interpreted with the following in mind: they are in many respects comparative, measured on the same BH meter and consequently characteristics attributable to the electrical characteristics of the meter are a common factor in all the drawings. In general, this is a minor factor. Most useful BH meters will produce very similar curves. Moreover, in making such pictures, as shown in FIGS. 2, 5 and 7, the distance from the origin (zero field point) to the peaks should be not more than about one-third of the distance from the origin to the maximum applied field. This is to assure that a particular angular function tending to "fatten" these peaks is made negligible.

Figure 2:
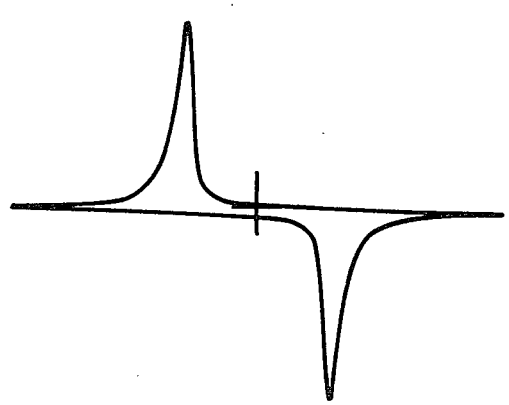
Figure 4:
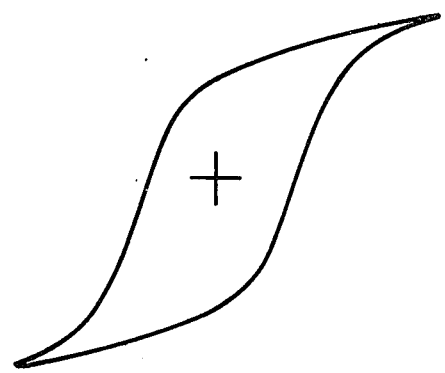
FIGS. 4 and 5 are similar to 2 and 3 but are descriptive examples of samples representative of applicant's best efforts before the making of the present invention.
Figure 5:
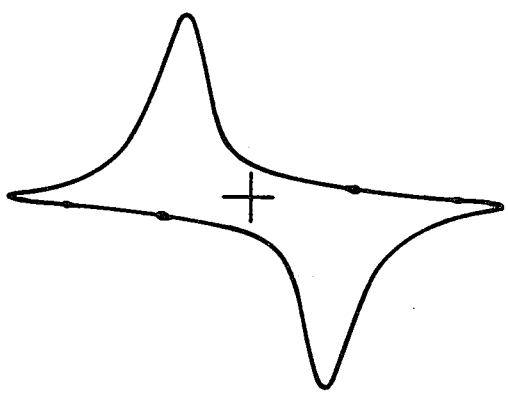

However, once these facts are realized, the drawings in FIGS. 2, 5 and 7 can be used to define highly advantageous and novel features of the invention.

$\Delta H$, peak-spread width at 50% of the peak height, over H, the distance from origin of the curve to the vertical line from the center of the peak. It is believed no acicular based particulate material known to the prior art has ever had a value of ($\Delta H/H$) of less than about 0.75. Yet the value of the material of Example 19 is about 0.62. Similar improvements are generally assignable to acicular products of the invention.

Making Magnetic Tape

The metal powders produced by the processes of this invention may be advantageously incorporated into magnetic tape utilizing many different polymer systems. However, in order to obtain a favorable loading it is believed to be most desirable to use pre-polymerized urethane resin systems. One such system would comprise 77 parts by weight of the metal powder product of Example 9, 2 parts soya lecithin, 19 pounds of the pre-polymerized polyurethane resin sold under the trade designation Estane 5707 by B.F. Goodrich Co., and as described in U.S. Pat. No. 2,871,218 to Schollenberger. Other additives would normally be added. These additives are known to those generally skilled in the art, and include fungicides, and the like. Two parts by weight of butoxyethyl stearate and 0.1 part by weight of diphenyl mercury would be suitable adjuvants for the formulation given above. The formulation when adequately mixed would be coated along a substrate such as a polyethylene terephthalate polymer film substrate, dried and slit for winding onto spools: all such processes are well known in the art.

Although the advantages of the ferromagnetic powders manufactured according to the invention can be achieved without supplemental treatment or compounding, it is noted that there will be some applications wherein formation of a suitable magnetic tape product will make it advantageous to add certain other magnetic powder thereto, e.g. ferromagnetic metal oxide powders or doped metal oxide powders to act as dispersing aids. Nevertheless, one advantage of the invention disclosed herein is that one may substantially avoid use of additives which contain non-ferromagnetic atoms (which usually either increase the crystalline anisotropy, decrease the magnetic moment or interfere with the chemical stability of the resulting particulate mass) and still achieve a recording medium of extraordinary quality.

Distribution of Switching Fields

A particularly advantageous feature of the invention is the ability to avoid unwanted magnetic switching in the magnetic fields of relatively small magnitude, i.e. in fields of from 0 to 200 oersteds. In a typical sample, there may be an absence of any significant switching below 200 oersteds, then be a significant amount of switching by the time the field is increased to 250 oersteds, and—finally—90% of the particles will switch when the field reaches the 500-oersted level.

This distribution of switching fields may differ somewhat as the formulation of morphology of particular products differs but the principle discussed in this paragraph relates in general to the favorable attribute of those particles of the invention which lack any significant switching over at a higher field. This feature makes the particles suitable for use in some magnetic memory applications wherein, say, very little switching is desirable at one field and the switching takes place with an increased field. This attribute is particularly important in avoiding print-through in reeled magnetic tape.

Another interesting application of particles having this advantageous switching characteristic is current-limiting transformer. For example, a transformer core would consist of particles of the type being discussed. The primary winding would be in an electrical circuit. As current is changed in the circuit, there would be no response to the presence of the core material as long as the current was not such as to induce a field of, say, 200 oersteds. However, when the current rises above a pre-selected value (determined by the number of windings of dimensions of the core) the field would exceed 200 oersteds and, at this point, the particles would begin to switch. It is only when this switching begins that the transformer makes its "appearance" in the circuit. The transformer would be fully operable by the time the field strength reached 500 oersteds. The secondary windings of the transformer could go to a resistive element which could serve to dissipate energy. On the other hand, a secondary element might consist of a feedback route to moderate the signal in the primary electronic circuit. A third possibility would be to have the secondary windings connected to an alarm bell or other such signal device.

Such a current-limiting transformer has a great many applications. It could be used to limit current and would have advantages over the fuse-type devices used today. Fuse-type devices shut down apparatus, in effect destroying the circuits.

Figure 3:
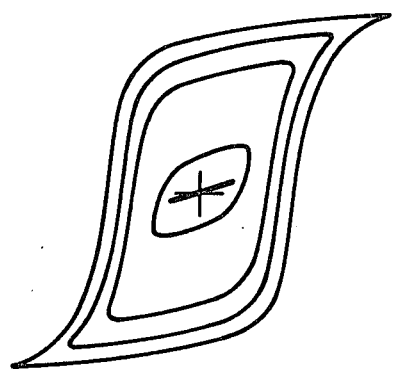
FIGS. 1 through 3 show typical hysteresis curves of a novel magnetic powder produced by the process of the invention as described in Example 19.

FIG. 3 discloses a series of hysteresis loops of one such material (that described in Example 18), a cobalt-based particulate material, which would be incorporated into such a core for use in the transformer described above. The central diagonal line was taken at 200 oersteds applied field. The smaller loop around the diagonal line was measured at a field of 250 oersteds, then, reading out from the center, the next sequential loops were measured at 500, 750, and 1,000 oersteds applied magnetic fields.

The distribution of switching fields plots the histogram of the number of particles which begin switching in a given increment of applied field. The coercive force of the group of particles is a measure of a weighted average of where the particles switch, but coercivity does not provide any information as to how the data is distributed around the average value. The histogram of FIG. 3 presents this distribution data. For magnetic recording use, the distribution of switching fields needs to be sharply distributed. A broad distribution causes severe problems in the design of the recording head and in the design of equalization electronics.

Another advantageous property of the process and novel powders produced thereby is the ability to provide powders having the extraordinarily favorable magnetic properties, mentioned elsewhere in this specification, and also exhibiting an extremely favorable $dM/dt$ curve. This curve (as indicated in FIG. 2) exhibits the unintegrated value of the magnetic moment (M) as a function of time. It is distinguished from the hysteresis loop of FIGS. 1, 4 and 6 in that the hysteresis loop of these curves represents the integrated value of M. For many applications, a $dM/dt$ curve that is sharply peaked, as opposed to a curve that is more gradually peaked, is thought to be particularly desirable. For example, in high-frequency magnetic recording, a curve which peaks and drops sharply and approaches its terminal points in a nearly horizontal direction is favored.

In this specification, the particular advantage of the claimed processes will often be most clearly identified by the magnetic properties of powders produced thereby. Applicants believe that such magnetic properties result from the particular order, molecular or atomic or crystalline, which the processes allow to be imparted to the material being described and to the uniform morphology of the resultant powder. However, it should be realized that even when the nature of the particle is not adequately measured by magnetic means (say, when the particle is largely non-magnetic in properties) an advantageous morphology or order is still contributed by the processing technique. Thus, such an order may contribute good optical properties to a pigment, good chemical-activity properties to a catalyst, or the necessary size, shape and crystalline uniformity to a powder to be used in coating or alloying processes.

Moreover, within the field of magnetic particles, it should be realized that such terms as "high squareness", "high coercivity", and the like are not absolute, but depend upon the particular metallic morphology being measured. Thus, applicants' ability to achieve squarenesses over, say, 0.70 in cobalt-based systems and to obtain such predominant shape anisotropy is illustrative of a general process capability of favorably controlling the particle size distribution and the crystalline structure of the particles being measured. This capability is new and should be recognized to have value even in systems where the results cannot be so dramatically shown to be novel as they can be in magnetic systems.

As a general proposition, it appears that crystals formed according to the invention, i.e. formed by the use of complexing agents or by the use of seed crystals which have been formed by the use of complexing agents, can themselves serve as seed crystals for propagation of further crystals having many of the advantages of the initially-formed crystal products. Of course, as the sequence of using seed crystals in subsequent batches proceeds, the seed crystals become larger and so do the crystal products formed therewith. But, for applications where very small size of the organometallic salt product is not necessary, there are compensating advantages. For example, squareness of the metal produced from the larger particles so produced appears to be even more favorable than that of earlier-produced smaller particles.

Illustrative Examples of the Invention

In order to point out more fully the nature of the present invention, the following working examples are given as illustrative embodiments of the present process and products produced thereby.

Unless otherwise specified, the specific examples disclosed below are carried out according to the following general procedure:

The precipitation is carried out in a 1,000 ml Erlenmeyer flask with four baffle-type indentations molded at 90 angular degree intervals around the base of the flask. Agitation is achieved by a magnetic stirring bar about 1.6 inches long and 0.5 inches in diameter.

The addition of solutions to the flask is accomplished through a funnel. The times of addition are longer as the viscosity of the solution being added increases.

Cobalt nitrate is used as the cobalt source but other such water-soluble cobalt salts as the acetate, chloride or sulfate are generally useful. The commercial varieties of these salts normally contain 3% of nickel based on the weight of cobalt. Experiments have indicated there is little or no advantage to the use of pure cobalt salts.

The water is used as deionized water processed through a standard commercial laboratory deionizer. A colorless commercial syrup is used as a source of sugar complexing agent. It is that material sold under the trademark Karo by Best Foods of Englewood Cliffs, New Jersey and is referred to hereinafter as Karo. It is formed principally of the type that digests to dextrose units. When sucrose is specified, ordinary sugar from any grocery store is used. Other reactants are utilized in their ordinary commercial form. The methanol is Reagent Grade, but such purity is not required. The ethanol is denatured ethanol. The glycerine is U.S. Pharmacopeoia grade, but again this purity is probably not required.

The organometallic salts, the preparation of which is disclosed below are coated with a resin and decomposed as follows:

The organometallic salt filter cake is air dried after washing and rewetted with isopropanol. A polyamide resin, sold under the trademark "Resymide 1125" by RESYN Corporation of Linden, New Jersey (and hereinafter referred to as "Resymide"), is dissolved in isopropanol. A quantity of the resin is used which is about 7% of the weight of the metal in the organometallic compound to be coated. The isopropanol suitably contains a concentration of about 10% resin. A thin slurry of the organometallic salts in the resulting liquid is formed and the isopropanol is evaporated as the slurry is stirred. The resulting dry powder is a mass of resin-coated particles ready for reduction.

In general, the reduction is carried out by placing the powder in sample boats containing eight different compartments. (Usually a different sample is in each compartment to facilitate comparative testing.) The sample boats are sealed in tubes having gas inlet and gas outlet ports, then placed in an oven, with conduits to both the outlet and inlet port extending from the oven to a gas-supply source and a gas exhaust system, respectively. The tubes are purged with $N_2$; then the oven temperature is set for 650° F. and a gas mixture of 20% hydrogen and 80% nitrogen is passed through the tubes at the rate of 40 cc per minute. Within about 45 minutes, $CO_2$ evolution starts. After the rate of $CO_2$ evolution peaks and drops to less than 0.01% by volume of the offgas, the tube is purged with nitrogen, and removed from the furnace. After cooling to room temperature—this usually takes an hour or so—a mixture of 3% oxygen and 97% nitrogen is passed through the tube. This gas mixture is usually allowed to run for several hours but the exact time, or even the exact composition, is not particularly critical.

Then the reacter is purged with air for two hours and opened. The samples are removed and are ready for analysis.

Usually a sample from a control batch of oxalate is fired with each eight-sample load as a means to confirm the reproducibility of the reduction process.

EXAMPLE 1

A quantity of 25.2 grams of oxalic acid dihydrate is dissolved in a mixture of 250 grams of Karo and 150 grams of water to form a first solution. To this first solution is added a second solution of 29.1 grams of cobalt nitrate hexahydrate in 100 grams of Karo and 50 grams of water. This addition is made over a period of about 30 minutes.

After the addition is completed, stirring is continued for an additional 30 minutes.

The mixture was filtered and washed two times with distilled water at 60° C. The filter cake, beige initially, turned pinkish in color on being washed with the water. Next the precipitate is washed in acetone. A sample is collected for a microscopic inspection; the remainder of the precipitate is resin coated and reduced to metal.

EXAMPLE 2

A procedure similar to that of Example 1 was followed excepting the first solution was comprised of 25.2 grams oxalic acid dihydrate, 200 grams of sucrose and 200 grams of demineralized water. The solution added to the first solution, through a funnel and over a period of about 13 minutes, was formed of 29.1 grams of cobalt nitrate hexahydrate in 75 grams sucrose and 75 grams of water.

Samples were taken as indicated in Example 1. After the precipitation of the cobalt oxalate salt, it was filtered, washed and reduced to form a metal powder more fully described in Table A.

The following examples were carried out, according to the general procedures of Example 2, to form metallic powders. Properties of these metals and the organometallic salt precursor are given in Table A.

EXAMPLE 3

| Solution 1 | | | Solution 2 | | |
|---|---|---|---|---|---|
| Oxalic acid dihydrate | 25.2 | gm | Cobalt nitrate hexahydrate | 29.1 | gm |
| glycerine | 200 | gm | glycerine | 75 | gm |
| water | 200 | gm | water | 75 | gm |

Addition time was 6 minutes and 9 seconds.

EXAMPLE 4

| Solution 1 | | | Solution 2 | | |
|---|---|---|---|---|---|
| Oxalic acid dihydrate | 25.2 | gm | Cobalt nitrate hexahydrate | 29.1 | gm |
| ethylene glycol | 200 | gm | ethylene glycol | 75 | |
| water | 200 | gm | water | 75 | |

Addition time was 5 minutes and 45 seconds.

EXAMPLE 5

| Solution 1 | | | Solution 2 | | |
|---|---|---|---|---|---|
| Oxalic acid dihydrate | 25.2 | gm | Cobalt nitrate hexahydrate | 29.1 | gm |
| ethanol | 125 | gm | ethanol | 50 | gm |
| water | 125 | gm | water | 50 | gm |
| Karo | 150 | gm | Karo | 50 | gm |

The addition took 10 minutes and 4 seconds. The mixing action was relatively poor because of the viscosity of the mix.

EXAMPLE 6

| Solution 1 | | | Solution 2 | | |
|---|---|---|---|---|---|
| Oxalic acid dihydrate | 25.2 | gm | Cobalt nitrate hexahydrate | 29.1 | gm |
| acetone | 125 | gm | acetone | 50 | gm |
| water | 125 | gm | water | 50 | gm |

| Solution 1 | | | Solution 2 | | |
|---|---|---|---|---|---|
| Karo | 150 | gm | Karo | 50 | gm |

Again, the addition took about 6 minutes.

EXAMPLE 7

| Solution 1 | | | Solution 2 | | |
|---|---|---|---|---|---|
| Oxalic acid dihydrate | 25.2 | gm | Cobalt nitrate hexahydrate | 29.1 | gm |
| water | 375 | gm | water | 140 | gm |
| Karo | 25 | gm | Karo | 10 | gm |

Solution 2 was added to Solution 1 in a little less than 5 minutes. The acicularity of the oxalate increased and, consequently, the bulk density dropped.

EXAMPLE 8

| Solution 1 | | | Solution 2 | | |
|---|---|---|---|---|---|
| oxalic acid dihydrate | 25.2 | gm | cobalt nitrate hexahydrate | 29.1 | gm |
| Karo | 400 | gm | Karo | 120 | gm |
| water | 100 | gm | water | 30 | gm |

It took about 37 minutes to add Solution 2 to Solution 1. The stirring was sluggish because of the high viscosity.

The product had a low bulk density, and less acicularity.

EXAMPLE 9

| Solution 1 | | | Solution 2 | | |
|---|---|---|---|---|---|
| oxalic acid dihydrate | 25.2 | gm | cobalt nitrate hexahydrate | 19.4 | gm |
| isopropanol | 125 | gm | ferrous sulfate heptahydrate | 9.3 | gm |
| water | 125 | gm | isopropanol | 50 | gm |
| propylene glycol | 75 | gm | water | 50 | gm |
| ethylene glycol | 75 | gm | propylene glycol | 25 | gm |
| | | | ethylene glycol | 25 | gm |

Addition time was about 6.5 minutes.

TABLE

PROPERTIES OF POWDERS

| Example No. | 1 | 2 | 3 | 4 | 5 | 6 | 7 | 8 | 9 |
|---|---|---|---|---|---|---|---|---|---|
| Specific Magnetic Moment | 125 | 117 | 122 | 118 | 119 | 114 | 119 | 110 | 96 |
| Coercive Force, Room Temp. | 770 | 783 | 715 | 799 | 1020 | 1020 | 730 | 773 | 1010 |
| Coercive Force, Liq. $N_2$ Temp. | 1344 | 1480 | 1340 | 1400 | 1690 | 1848 | — | — | 1380 |
| Ratio Liq. $N_2$/Room Temp. | 1.75 | 1.89 | 1.87 | 1.75 | 1.66 | 1.81 | — | — | 1.37 |
| Squareness | .78 | .78 | .78 | .81 | .79 | .80 | .76 | .73 | .63 |
| Particle Size | | | | | | | | | |
| Length, Ave | 10.6 | 9.3 | 10.1 | 7.5 | 3.5 | 6.3 | 7.9 | 15.1 | — |
| Std. Dev. | 4.6 | 4.1 | 2.7 | 3.9 | 1.0 | 1.6 | 3.3 | 9.1 | — |
| Width, Ave | .82 | .59 | .71 | .41 | 0.20 | .41 | 1.34 | 1.37 | — |
| Std. Dev. | .44 | .36 | .22 | .19 | .04 | .07 | .67 | .47 | — |
| L/D Ratio, Ave | 14.6 | 18.4 | 15.4 | 20.2 | 17.9 | 15.8 | 7.95 | 11.5 | — |
| Std. Dev. | 5.8 | 10.5 | 5.6 | 11.4 | 5.0 | 4.9 | 4.6 | 5.4 | — |
| Min. Value | 6.2 | 6.7 | 8.7 | 7.1 | 10.0 | 10.6 | 3.75 | 4.5 | — |
| Max. Value | 29.4 | 54.0 | 27.4 | 55.4 | 33.3 | 29.6 | 14.9 | 24.3 | — |

EXAMPLE 10

| Solution 1 | | | Solution 2 | | |
|---|---|---|---|---|---|
| oxalic acid dihydrate | 9.8 | gm | cobalt nitrate hexahydrate | 14.2 | gm |
| water | 120 | ml | nickel nitrate hexahydrate | 2.0 | gm |
| Karo | 280 | ml | water | 140 | ml |
| | | | Karo | 140 | ml |

Solution 2 was added dropwise to Solution 1. The resultant precipitate was filtered, washed with hot water, then isopropanol, then dried. It was then coated with a solution of phenoxy resin dissolved in tetrahydrofuran. This resin is sold under the trademark PKHH by Union Carbide. A quantity was used equal to 7% of the weight of the metal in the salt. The salt was reduced according to the general procedure set forth above.

The resulting metal powder had a coercive force of 640 oersteds, a squareness of 0.76 and a magnetic moment of 109 emu per gram.

EXAMPLE 11

| Solution 1 | | | Solution 2 | | |
|---|---|---|---|---|---|
| oxalic acid | 25.2 | gm | cobalt nitrate hexahydrate | 29.2 | gm |
| water | 500 | ml | ethylene glycol | 25 | ml |
| | | | Karo | 25 | ml |
| | | | water | 50 | ml |

Solution 2 was added dropwise to the oxalic acid-containing solution over a period of one hour. The precipitated cobalt oxalate was easily filtered, and washed as in Example 1. Before being reduced, the oxalate was subjected to optical analysis by a scanning electron microscope. The observed results:

| | Average | Max | Min | Std. Dev. |
|---|---|---|---|---|
| Length, microns | 58.5 | 99.9 | 17.1 | 22.8 |
| Diameter, microns | 2.3 | 3.6 | 1.6 | 0.49 |
| L/D ratio | 24.3 | 42.1 | 10.6 | 8.6 |

A very readily filterable oxalate with a high degree of acicularity was obtained.

EXAMPLE 12

| Solution 1 | | | Solution 2 | | |
|---|---|---|---|---|---|
| oxalic acid dihydrate | 25.2 | gm | cobalt acetate tetrahydrate | 25 | gm |
| water | 335 | ml | glacial acetic acid | 1 | ml |
| ethanol | 165 | ml | Karo | 85 | ml |
| | | | water | 45 | ml |

After Solution 2 was added to Solution 1, an organo-metallic salt, i.e. cobalt oxalate was precipitated, washed, dried, coated and reduced as has been described above.

The resulting magnetic cobalt particles have a coercive force of 1212 oersteds, a squareness of 0.74 and a specific magnetic moment of 108. The coercive force at liquid nitrogen temperature was 1,440 oersteds, showing the relatively small crystalline anisotropy effect.

EXAMPLE 13

| Solution 1 | | | Solution 2 | | |
|---|---|---|---|---|---|
| oxalic acid | 25.2 | gm | cobalt nitrate hexahydrate | 29.2 | gm |
| water | 400 | ml | tartaric acid | 30 | ml |
| | | | water | 200 | ml |

Solution 2 was added dropwise to Solution 1 with vigorous stirring. Acicular crystals of the resulting cobalt oxalate were formed. The crystals were highly permeable to liquid and were easily washed.

A sample of thirty crystals was measured by electron photomicrograph. Average length was 6.47 microns (std. deviation 2.3, range 1.7 to 10.7 microns). Average width was 0.447 microns (std. deviation 0.12, range 0.78 to 0.28). The average length:diameter ratio was 15.1 (std. deviation 5.98, range 47 to 28.3).

Coercivity of the mass of particles was 886, the magnetic moment was 128 and a squareness of 0.803.

EXAMPLE 14

A seed crystal mixture was prepared according to the following procedure:

| Solution 1 | | Solution 2 | | |
|---|---|---|---|---|
| Cobalt acetate | 25 gm | oxalic acid dihydrate | 25.2 | gm |
| citric acid | 25 gm | Karo | 150 | gm |
| water | 50 gm | water | 150 | gm |
| Karo | 50 gm | ethanol | 150 | gm |
| ethanol | 50 gm | | | |

Solution 2 is added slowly at 18° C. into Solution 1 in a 1 liter baffled Erlenmeyer flask equipped with a magnetic stirring bar. Initially stirring is so vigorous that bubbles of air are whipped into the oxalic solution. When about a third of the Solution 2 is added, the material will be so viscous that it will no longer vortex. The agitator is stopped momentarily to clear the solution of air bubbles, then stirring is resumed. The cobalt is introduced about one-eighth inch above the magnetic stirring bar. As the remainder of the cobalt is added the mix becomes a very viscous suspension. A 200 milliliter sample of this suspension is filtered on a Buchner vacuum filter using Whatman No. 5 filter paper. The crystals were washed with 400 milliliters hot water and then with 200 milliliters acetone. The crystals lift off the filter paper as a paper-like sheet. These crystals were difficult to photograph and measure, but size data in included in Table I and is based on scanning electron microscope (SEM) pictures taken at 10,000X.

A 5 gram sample of these crystals was coated with .113 grams of Resymide in isopropyl alcohol. The alcohol was evaporated and the powder placed in a tube furnace sample boat. It was reduced in 20% hydrogen and 80% nitrogen until the $CO_2$ in the vent gas dropped below 0.04%. It was cooled to 20° C. under nitrogen and then exposed to 3% oxygen in nitrogen for 16 hours. The sample was next exposed to dry air for two hours and then analyzed magnetically. Data is given in Table B.

| Solution 1 | | | Solution 2 | | |
|---|---|---|---|---|---|
| cobalt nitrate hexahydrate | 29.1 | gm | oxalic acid dihydrate | 25.2 | gm |

-continued

| Solution 1 | | Solution 2 | | |
|---|---|---|---|---|
| water | 150 gm | water | 250 | gm |

Solution 2 was made in a 1000 milliliter baffled Erlenmeyer flask equipped with a magnetic stirrer. When the oxalate was dissolved, 2 milliliters of the seed solution in Example 14 were added to Solution 2. The Solution 1 was added slowly to the seed-bearing mixture. A beige-pink precipitate resulted. This material was filtered, washed with 600 milliliters hot water and 200 milliliters of acetone. The crystals were sampled for SEM photographs. 10 grams of this oxalate was coated with 0.225 grams Resymide and reduced according to the procedure described in Example 1. Data on the metal is given in Table B.

EXAMPLE 16

The experiment was identical to Example 15, except that 10 milliliters of seed mixture was added to Solution 2. Data on the metal is given in Table B.

EXAMPLE 17

The experiment was identical to Example 15, except that 50 milliliters of seed mixture was added. Data on the metal is given in Table B.

EXAMPLE 18

The experiment was identical to Example 15, except that 200 milliliters of seed mixture was added. Data on the metal is given in Table B.

These crystals were filtered in a Buchner funnel, washed with 600 milliliters of hot water, rinsed with acetone and dried. They were weighed, wetted with isopropanol and coated with resymide in isopropanol at a level corresponding to 7 weight % based on metal content. The isopropanol was dried and the particles reduced in a tube furnace as before. These particles had a:

| | |
|---|---|
| Specific magnetic moment | 138 emu/gram |
| Coercive force | 659 oersteds |
| Squareness | 0.84 |

Figure 1:
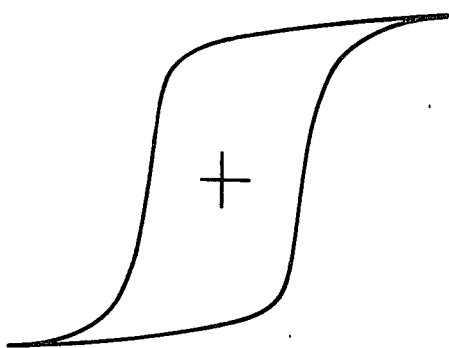

Drawings of the hysteresis loop and of the $dM/dt$ curves are shown in FIGS. 1-3. Samples of this material were stored in a humidity oven (Tenney Engineering, Union, New Jersey, Model TMTH 0200) at 66° C. and 50% relative humidity for 160½ hours. After this exposure, the specific magnetic moment was found to be 112 emu/gram.

The material comprises about 18% nickel, 18% iron and 64% cobalt and has an extraordinary combination of corrosion-resistance and magnetic properties.

EXAMPLE 20

A seed crystal suspension was prepared as shown in Example 14. 100 milliliters of suspension was placed in a 1000 milliliter baffled Erlenmeyer flask. A solution of 25 grams of oxalic acid dihydrate in 250 grams of water was added slowly while stirring. An additional 50 milliliters of water was used to rinse the remaining oxalic Table B Metals of Examples 14 – 18

| | Control | 14 | 15 | 16 | 17 | 18 |
|---|---|---|---|---|---|---|
| Milliliter of Seed Added | None | (All Seed) | 2 | 10 | 50 | 200 |
| Coercive Force, oe. | 805 | 1087 | 758 | 840 | 823 | 1038 |
| Squareness | .75 | .74 | .79 | .83 | .82 | .77 |
| Specific Magnetic Moment | 115 | 106 | 102 | 120 | 110 | 121 |
| Length, Microns | | | | | | |
| Average | 8.7 | 2.5 | 9.4 | 7.7 | 7.05 | 2.38 |
| Maximum | | | 16.5 | 20.5 | 10.6 | 4.1 |
| Minimum | | | 3.8 | 1.6 | 4.4 | 1.1 |
| Std. Dev. | 3.4 | | 3.3 | 3.9 | 2.0 | .85 |
| Diameter, Microns | | | | | | |
| Average | 1.5 | .19 | 1.2 | .75 | .53 | .35 |
| Maximum | | | 1.84 | 1.3 | .83 | .45 |
| Minimum | | | 0.49 | .37 | .34 | .27 |
| Std. Dev. | .66 | | .38 | .27 | .13 | .05 |
| L/D Ratio | | | | | | |
| Average | 6.4 | 13.3 | 8.33 | 11.4 | 13.9 | 6.8 |
| Maximum | 10.0 | | 14.8 | 30.8 | 23.3 | 12.2 |
| Minimum | 2.4 | | 3.4 | 2.3 | 7.6 | 3.0 |
| Std. Dev. | 1.8 | | 3.0 | 6.9 | 4.4 | 2.5 |
| N | | | 18 | 26 | 16 | 17 |

EXAMPLE 19

A seed crystal was prepared as in Example 14. 100 milliliter of seed suspension was placed in a baffled 1000 milliliter Erlenmeyer flask. A solution containing 25.2 grams of oxalic acid dihydrate and 400 grams of water was added slowly to the seed crystals with agitation. Next a solution containing 18 grams of cobalt nitrate hexahydrate, 5 grams of ferrous sulfate heptahydrate and 5 grams of nickel nitrate hexahydrate in 150 grams of water was added slowly with agitation, 10 minutes being required for complete addition. A pearlescent suspension results which is light yellow in color.

crystals into the flask. A suspension of 11.8 grams of commercial cobalt carbonate in 200 milliliters of water was added slowly, 7 minutes being required. Bubbles of gas rise to the top gradually as the cobalt carbonate is added. The mixture was allowed to stir for 30 minutes at 23° C. A light pink colored precipitate is formed. 100 milliliters of this first suspension was set aside and the remainder was filtered, washed, rinsed with isopropanol, dried, weighed, coated with 7% resymide based on cobalt and reduced to metal. This sample is labeled A in the table of magnetic properties.

The 100 milliliters of the first suspension was mixed with 25 grams of oxalic acid solution and then 11.8 grams of cobalt carbonate suspension was added. The resulting suspension of precipitate was thick, but was more tan in color than the previous one. 100 milliliters of this second suspension was also set aside and the remainder filtered, coated, and reduced to metal. This sample is labeled B. The 100 milliliters of second suspension was used as above to make a precipitate which was reduced to metal powder C; a third 100 milliliter sample of suspension was reserved during the procedure. This precipitate was brownish in color. 100 milliliters of the third suspension was used to make a precipitate which was brownish in color and which was reduced to metal powder "D". Table C shows the properties of the metals formed.

Table C

| Metal Powder | Coercive Force | Squareness | Magnetic Moment |
|---|---|---|---|
| A | 767 | 0.70 | 145 |
| B | 704 | 0.72 | 146 |
| C | 720 | 0.75 | |
| D | 711 | 0.77 | 143 |

EXAMPLE 21

A seed crystal was prepared as described in Example 14, but using alanine in place of citric acid. A quantity of 100 milliliters of the resulting alanine seed crystal suspension was added to a solution containing 25.2 grams of oxalic acid dihydrate and 400 milliliters of water. A solution of 29.1 grams cobalt nitrate hexahydrate in 200 milliliters of water was added slowly to the oxalic acid seed crystal mixture. A thick pink precipitate resulted which was filtered, washed with hot water, dried with isopropyl alcohol, weighed, coated with Resymide and reduced in the tube furnace as described in Example 1. The magnetic properties of this powder were measured to be as follows: 118 emu/gram specific magnetic moment; 850 oersteds coercive force; and 0.78 squareness.

EXAMPLE 22

A seed crystal was prepared as follows: a solution was prepared of 25.2 grams oxalic acid dihydrate, 150 grams Karo syrup, 150 grams denatured ethyl alcohol, and 150 grams water. To this solution was added a solution containing 29 grams cobalt nitrate hexahydrate, 32 grams ammonium nitrate, 50 grams Karo, 50 grams denatured ethyl alcohol, and 50 grams of water. A suspension of a very viscous pink precipitate resulted. A quantity of 100 milliliters of this suspension was added to a solution containing 25 grams of oxalic acid dihydrate and 400 milliliters of water in a 1 liter, baffled Erlenmeyer flask equipped with a magnetic stirrer. To this mixture was added a solution containing 29.1 grams of cobalt nitrate hexahydrate and 200 milliliters of water. A pink precipitate resulted which was filtered, washed with hot water, washed with alcohol and dried. The sample was weighed and the usual quantity of Resymide was added in isopropyl alcohol. The resulting solution was dried and fired in the tube furnace as described in Example 1. The magnetic properties of this material were found to be: specific magnetic moment of 126 emu/gram; coercive force of 625 oersteds and a squareness of 0.81.

Catalysts

As has been indicated elsewhere in this specification the processes of the invention are useful in forming novel particles having use outside the magnetic applications areas. Many of these areas have very limited theoretical basis for explaining the exact properties which contribute to the utility. Nevertheless, applicants' experience clearly indicates that the ordered arrangement and uniformity of particles made possible by their complex-agent-modified seeding process is directly responsible for whatever esoteric balance of properties result in the extraordinary properties of such materials.

One of the particular advantages of the invention is that it provides means to manufacture novel and improved metal catalysts which have excellent activity and can be duplicated with excellent predictability.

One of the well-known catalysts now used in many chemical processes is the so-called Raney catalyst. This catalyst is expensive and is not stable. Consequently, it is usually freshly prepared each time it is used. Some investigators have claimed stability of the Raney-type catalyst if the material is kept in a refrigerated condition and under dry alcohol. However, even under these conditions, catalytic activity would last only a couple of days. From the foregoing it is clear that it would be highly desirable to provide an improved, more stable and more effective catalyst to replace the conventional Raney-type.

EXAMPLE 23

A seed crystal was prepared by dissolving 25 grams of cobalt acetate tetrahydrate, 25 grams of citric acid, and 50 grams of the dextrose syrup sold under the trade name Karo in 50 grams of water and 50 grams of denatured ethanol (ethyl acetate and other alcohols were used as the denaturants in this commercially-obtained denatured alcohol). A second solution was prepared containing 25.2 grams oxalic acid dihydrate, 150 grams of ice, 150 grams of the aforesaid denatured ethanol, and 150 grams of the aforesaid dextrose solution. The second solution was placed in a 1 liter Erlenmeyer flask equipped with a magnetic stirrer. The first solution was then added slowly to the second solution while stirring the mixture. A very thick viscous suspension of cobalt oxalate seed crystals resulted.

A quantity of 50 ml of this seed crystal suspension was placed in a second one-liter baffled Erlenmeyer flask which contained 25 grams of oxalic acid dihydrate dissolved in 500 ml of water.

Thereupon, a nickel-bearing solution was prepared containing 27.6 grams of nickel nitrate hexahydrate in 150 ml of water; 100 ml of this solution was added slowly to the contents of the second Erlenmeyer flask. Vigorous stirring was maintained throughout the addition.

The excess of the solution over and above the 100 milliliters added to the second Erlenmeyer flask was mixed with a solution containing 1.25 grams zinc nitrate and 50 milliliters of water. This mixture was then added to the ultimate suspension of nickel oxalate particles with agitation. Next, the suspension was filtered, washed with 500 milliliters of hot water, then with 250 milliliters of acetone, and then dried. The resulting particles were reduced to metal particles by heating in a tube furnace at 650° F. while passing a mixture of 20% hydrogen and 80% nitrogen gas through the furnace until the evolution of $CO_2$ stopped.

The sample was allowed to cool in the presence of a 20% hydrogen-80% nitrogen mixture for 16 hours. It was then covered with dry isopropyl alcohol.

The specific magnetic moment, i.e. sigma value, was found to be 59 emu per gram. The coercive force was 241 oersteds, the squareness was 0.56.

One gram of this powder was mixed with 50 milliliters of a 7% solution of cinnamic acid in isopropanol in a reactor known in the art as a Parr hydrogenator. This device was charged to a pressure of 50 psig at room temperature and was agitated with shaking for one hour. After this time, a two milliliter sample of the contents of the hydrogenator was taken and titrated with bromine solution until a stable color was achieved for a period of five minutes after the last addition of bromine. 83% of the cinnamic acid was found to have been hydrogenated.

EXAMPLE 24

The process described in Example 23 was repeated except 3.62 grams of aluminum sulfate was substituted for the zinc nitrate used in the foregoing example. The resulting metal powder had a specific magnetic moment of 64 emu per gram and a coercive force of 225 oersteds and a squareness of 0.48. On the hydrogenation of cinnamic acid carried out in the same method as described in the foregoing example, 66% of the acid was hydrogenated.

EXAMPLE 25

A seed crystal was prepared by forming a first solution of 25 grams cobalt acetate tetrahydrate, 25 grams citric acid, 50 grams of Karo syrup and 50 grams of water and 50 grams of denatured ethanol. This solution was aded slowly and with stirring to a solution which had been preprepared and was formed of 25.2 grams oxalic acid dihydrate, 150 grams ice, 150 grams denatured alcohol and 150 grams Karo. A very thick viscous suspension resulted. A quantity of 50 ml of this cobalt-oxalate seed material was added to a 1-liter baffled Erlenmeyer flask which already contained a solution of 25 grams of oxalic acid dihydrate in 400 ml of water.

Next, a solution was prepared by dissolving 27.6 grams of nickel nitrate hexahydrate in 150 ml of water. This solution was added slowly to the oxalic acid solution containing the suspended seed crystals. Vigorous agitation was maintained during the mixing procedure.

After the mixing was complete, the resulting suspension was filtered and the crystals were washed with 500 ml of hot water and 250 ml of acetone. These crystals were dried and reduced in a tube furnace at 20% hydrogen and 80% nitrogen for four hours, in which time the $CO_2$ in the off-gas was less than 0.02%. Then the tube furnace was cooled under 20% hydrogen—80% nitrogen mixture to room temperature. After the tube had been purged with nitrogen and opened, the particles were covered with dry isopropanol.

The resulting material had a specific magnetic moment of 36 emu per gram, a coercivity of 175 oersteds, and a squareness of 0.4. One gram of the powder was mixed with 50 ml of a 7% solution of cinnamic acid in isopropanol in a Parr hydrogenator. The material was processed and tested as has been described in the other examples. 34% of the cinnamic acid has been reduced during the hydrogenation procedure.

It is of particular interest that the illustrated catalysts had substantially constant activity at the time of their preparation and 29 days thereafter. During the 29-day period they were stored under isopropanol but in an environment between about 75° F. and 105° F. that was over 90° F. during a large part of that time. Thus these catalysts far outperform the Raney-type materials known in the art.

Dispersion — Strengthened Alloys

Another field of utility, not depending on ferromagnetic properties, yet advantageously advanced by the process of the invention is that relating to dispersion — strengthened alloys, e.g. those of the type described in National Aeronautical and Space Administration (NASA) publication SP5098. Thorium oxide, as other oxides, can be prepared by making a thorium oxalate by the process described herein and converting the oxalate, to thorium oxide. Oxide so produced will derive a uniformity of particle size and morphology from the acicular oxalates and, apparently for that reason are advantageous and economically useful in making dispersion-strengthened alloys.

Others skilled in the metallurgical art and, indeed those skilled in other such metal-oxide-utilizing art including the pigment — making art will recognize the value of the organmetallic salt-decomposing route for use in manufacture of oxides for many purposes.

Testing Methods

Some of the materials illustrated by Specific Examples have been tested as set out below. The results are in Table 2. The following comments are made on the various testing methods and parameters where such comments are believed to be necessary or convenient.

A. Specific Magnetic Moment

The specific magnetic moment, or sigma value, is the value of the saturation magnetic moment per unit, usually weight, of a magnetic material. It was measured on a vibrating sample magnetometer with a 4,000 oersted applied field. The instrument is calibrated directly in elecromagnetic units and is checked daily against a standard. The values of sigma are given in electromagnetic units per gram of material.

B. Coercivity

The coercive force of the samples was measured at 25° C. in a 60 cycle BH loop tracer with an applied magnetic field of 3000 oersteds. The values reported are in oersteds, magnetizing field strength at which the intrinsic flux density in the sample is zero when a sample of the magnetic material is in a symetrically cyclical magnetized condition. In the particles of the invention which are intended for magnetic tape, the coercive force largely reflects size and shape of the metal particles. The higher coercive force belongs to the smaller particles or the the more acicular particles.

C. Coercive Force at Liquid Nitrogen Temperature

The chief reason for this measurement is to get a comparison betwen coercive force at room temperature and at very low temperature. If the coercive force is controlled by shape anisotropy, there will be very little change in coercivity when the sample is cooled to liquid nitrogen temperature. If the coercive force is caused by crystalline anisotropy, the coercive force will change as the temperature to approximately the tenth power. This extremely large temperature coefficient makes it easy to detect materials whose coercive force is determined mainly by crystalline anisotropy. Crystalline anisotropy materials are undesirable in the manufacture of magnetic tape because the settings for bias, record current, etc. have to be changed as a function of temperature. There have also been a number of other problems encountered in the art with crystalline anisotropy-sensitive materials.

D. Squareness

Squareness of the BH loop is a measure of the remanent magnetization divided by the saturation magnetization. This is significant in magnetic recording particularly for long wavelength recording. Iron oxide has a squareness of 0.75 and is the currently used magnetic material for tape. Obviously the squareness ratio is a dimensionless number. These values are run on linseed oil emulsions of particles. The field causes the particles to align magnetically with the field. The oil is viscous enough that the particles switch rather than rotate.

In this application, the oil-metal emulsion is placed in a 6-millimeter glass tube, then inserted into the sample coil of a 60-cycle loop tester. Squareness is measured at 2000 oersteds applied field. Values measured this way agree to two significant figures with the values measured in oriented tape in the direction of orientation.

E. Distribution of Switching Fields

This is a measure of the uniformity of coervice force within a particulate sample. From data taken on the 60 cycle 5000 oersted BH loop tester, then we can prepare a graph of the remanent flux as a function of applied magnetic field. The slope of this curve, $d\phi r/dH$, defines the histogram of number of particles switching as a function of applied field. This histogram then reflects the particle size and shape. As the particle size gets smaller, the coercive force passes through a maximum. As the acicularity of the metal particles increases, the coercive force increases. So one can judge uniformity of size and shape from this measurement.

In actual practice, the metal particles are dispersed in a mixture of 10 grams of Nujol mineral oil and 90 grams of paraffin. About 1 gram of particles is mixed, with random stirring in 3 grams of melted wax to form a stiff paste. This is then forced into a 6 mm glass tube and cooled to freeze it and immobilize the particles. $\phi r$ is then measured as a function of the applied field from zero to 5,000 oersteds. For mathematical expedience, data is taken at each 200 oersted increment, and a parabola is fitted through the first three data points, then the slope of the parabola is calculated at an even value of the field near the midpoint of the parabola. The smallest point is then dropped and the next larger point is added. Then the parabola is again fitted and the slope is calculated. When all slopes are calculated, they are summed. Each slope is then divided by the sum of the slopes and the result multiplied by 100. This data is summarized on a table.

Salient features to look for are:

1. at low applied fields no particles should switch. This means no print through of recorded information from one layer of magnetic tape to the next. Additionally, it means that there are no very large particles capable of supporting more than one domain. Further, it means that there are no very small particles, called superparamagnetic particles.

2. very little switching should place at fields higher than 3,000 oersteds. One should note, though, that during the dispersion to make tape, the high end of this curve "cleans up" and presents less of a problem. The curve should be relatively sharply peaked, with the maximum value above 10%.

In general, the most advantageous ferromagnetic powders of the invention are those wherein the peak switching is 10% or above but advantageously 15% or higher, wherein less than 10% of the switching takes place at 50% of the peak switching field. All of the powders of Table D meet these criteria.

TABLE D

POWDER PROPERTIES
DISTRIBUTION OF SWITCHING FIELDS
OF METAL POWDER IN PARAFFIN WAX, %

| Field strength in oersteds | Example numbers | | | |
|---|---|---|---|---|
| | 1 | 5 | 6 | 9 |
| 0 | 0 | 0 | 0 | 0 |
| 200 | 1.08 | .36 | .36 | .15 |
| 400 | 1.79 | .37 | .22 | .46 |
| 600 | 10.04 | 1.82 | 1.17 | 2.15 |
| 800 | 18.42 | 5.89 | 5.13 | 4.19 |
| 1000 | 18.61 | 10.72 | 10.38 | 6.66 |
| 1200 | 14.63 | 14.63 | 14.89 | 10.84 |
| 1400 | 11.03 | 16.40 | 16.65 | 13.97 |
| 1600 | 9.08 | 14.83 | 15.15 | 14.28 |
| 1800 | 6.32 | 11.80 | 12.28 | 13.19 |
| 2000 | 3.92 | 8.34 | 9.12 | 11.09 |
| 2200 | 2.17 | 5.88 | 6.47 | 8.50 |
| 2400 | 1.14 | 4.33 | 4.20 | 6.71 |
| 2600 | 1.14 | 2.75 | 2.54 | 4.74 |
| 2800 | .63 | 1.88 | 1.42 | 3.07 |
| 3000 | 0 | 0 | 0 | 0 |

The chemical stability of the ferromagnetic particles of the invention is adequately measured by exposure to an environment of 50% relative humidity at 165° F. for 100 hours. Some products of the invention will retain 70% or more of their magnetic moment (sigma value) after this treatment. In addition to this chemical stability, the basic ferromagnetic properties of a class of novel materials produced by the process of the invention are as follows:

Minimum squareness of 0.72
Minimum Sigma value of 110
Minimum Coercivity of 500

It is emphasized that these are properties defining a family of novel ferromagnetic materials. In fact, substantially higher values can be achieved for each of these parameters as is specifically shown by the specific examples. Moreover, there are many advantageous, perhaps novel, powders produced by the process described herein which are not within the above family of materials. Their failure to be included within the group defined by the above list of properties is not to be interpreted as a failure to recognize their novelty or an intent to exclude them from the scope of the invention defined the claims appended to this specification.

It is, of course, to be understood that the foregoing examples are intended to be illustrative and that numerous changes can be made in the reactants, proportions, and conditions set forth therein without departing from the spirit of the invention as defined in the appended claims.

What is claimed is:

1. A process for making cobalt based metallic particles containing at least 50% cobalt, said process comprising the steps of
    1. selecting fasces-shaped metal-oxalate particles comprising said cobalt and consisting of rod like structures of substantially greater acicularity than said fasces-shaped particles, and
    2. reducing said salt to cobalt-based particles
        said cobalt-based particles being characterized by a magnetic squareness of at least 0.72 and a coercivity of at least 500 oersteds.

2. A process as defined in claim 1 wherein metal of said oxalate comprises about 18% iron, about 18% nickel and about 64% cobalt.

3. A process as defined in claim 1 wherein said fasces-shaped organometallic salt is formed by growth upon initially-precipitated cobalt oxalate seed particles.

4. A process as defined in claim 3 wherein said cobalt seed particle is characterized by a pinkish color when in its precipitation medium.

5. A process as defined in claim 2 wherein said fasces-shaped organometallic salt is formed by growth upon initially-precipitated cobalt oxalate seed particles.

6. A process as defined in claim 4 wherein said fasces-shaped organometallic salt is formed by growth upon initially-precipitated cobalt oxalate seed particles.

7. Cobalt-based particles formed by the process of claim 1.

8. Cobalt-based particles formed by the process of claim 3.

9. Cobalt-based particles formed by the process of claim 4.

* * * * *

UNITED STATES PATENT OFFICE
CERTIFICATE OF CORRECTION

Patent No. 4,004,917      Dated January 25, 1977

Inventor(s) Robert J. Deffeyes; Wesley R. Tyler

It is certified that error appears in the above-identified patent and that said Letters Patent are hereby corrected as shown below:

Column 3, line 68:    change "accularity" to --acicularity--;

Column 16, line 32:    underline "less";

Column 16, line 48:    insert --A-- after "TABLE";

Column 18, line 53:    change "in" (first instance) to --is--;

Column 18, line 65:    insert --EXAMPLE 15--;

Column 23, line 38:    change "aded!" to --added--;

Column 23, line 67:    change "has" to --had--.

Signed and Sealed this

Fourteenth Day of June 1977

[SEAL]

Attest:

RUTH C. MASON
*Attesting Officer*

C. MARSHALL DANN
*Commissioner of Patents and Trademarks*